United States Patent [19]
Kutschbach et al.

[11] Patent Number: 6,022,107
[45] Date of Patent: Feb. 8, 2000

[54] PROCESS AND SYSTEM FOR DETERMINING THE TOPOGRAPHY OF EYE REACTION SIGNALS

[75] Inventors: Ernst Kutschbach; Uwe Held, both of Chemnitz; Uwe Hoch, Gersdorf; Ralf Guenther, Crimmitschau; Manfred Stasche, Wiesbaden; Albrecht Hinkel, Gruenberg, all of Germany

[73] Assignee: Cindatec Ingenieurtechnische Dienste GmbH, Chemnitz, Germany

[21] Appl. No.: 09/117,611

[22] PCT Filed: Nov. 29, 1997

[86] PCT No.: PCT/DE97/02791

§ 371 Date: Apr. 6, 1999

§ 102(e) Date: Apr. 6, 1999

[87] PCT Pub. No.: WO98/24364

PCT Pub. Date: Jun. 11, 1998

[30] Foreign Application Priority Data

Dec. 2, 1996 [DE] Germany .................. 196 49 858

[51] Int. Cl.[7] ............................................. A61B 3/10
[52] U.S. Cl. ................................................. 351/200
[58] Field of Search .................................. 351/205, 206, 351/211, 212, 221, 246; 600/558

[56] References Cited

U.S. PATENT DOCUMENTS

| | | |
|---|---|---|
| 4,822,162 | 4/1989 | Richardson et al. . |
| 4,846,567 | 7/1989 | Sutter . |
| 5,233,373 | 8/1993 | Peters et al. . |
| 5,382,987 | 1/1995 | Sperling . |
| 5,539,482 | 7/1996 | James et al. . |
| 5,632,282 | 5/1997 | Hay ........................ 600/558 |

FOREIGN PATENT DOCUMENTS

WO92/03088 3/1992 WIPO .

OTHER PUBLICATIONS

B. Brown et al.: "Contrast and luminance as parameters defining the output of the Veris topograhical ERG", Ophthalmic & Physiological Optics, vol. 16, No. 1, Jan. 1996, pp. 42–48.

E.E. Sutter et al.: "The Field Topography of ERG Components in Man", Vision Research vol. 32, No. 3, 1992, pp. 433–446.

S. Parks et al.: "Comparison of repeatability of the multifocal electroretinogram and Humphrey perimeter", Documenta Opthalmologica, vol. 92, 1997, pp. 281–289.

Primary Examiner—George Manuel
Attorney, Agent, or Firm—Jordan and Hamburg LLP

[57] ABSTRACT

The purpose of the invention is to determine the topography of retinal reactions with high effectiveness and great certainty. In accordance with the invention, the problem is solved by generating a light-emitting image consisting of surface segments on a surface placed before the eye, and using complete extended m sequences, to brighten and darken the surface segments in each time interval. From the eye reaction signal, with the aid of the cross-correlation function, the reaction functions of the segments are calculated in each time interval, and the quality of the results is evaluated by forming some functions for each time interval. Only reaction signals evaluated as good are added up for the total result. The reaction signal of the eye is monitored for staying within limit values, and when errors are recognized, the m sequences are set back by a number of steps which can be preset, recognized errors in the reaction signal are replaced by the repetition. Each image is displayed in a first adjustable partial step and darkened during a second adjustable partial step.

27 Claims, 3 Drawing Sheets

PROCESS AND SYSTEM FOR DETERMINING THE TOPOGRAPHY OF EYE REACTION SIGNALS

The invention relates to a process and system for determining the topography of eye reaction signals, for which a luminous image is represented on a surface consisting of surface segments placed before the eye, where each surface segment is controlled to be bright or dark through a time function assigned to it and, at the same time, the total eye reaction is measured.

The topography determined for the eye reaction signals shows the objective sensitivity of the retina and thus provides information on the ability to see. With such examination, early recognition and evaluation of eye diseases, for example glaucoma, is possible. Above all, such examinations can detect partial defects in the retina.

There are many methods of examination, which work on a subjective basis, that is, in which the person examined evaluates the measurement by his statement. In all these methods, the patient is integrated into the measurement by making statements as to whether and how he experiences a certain stimulus.

The electroretinogram (ERG) has been established as an objective measuring procedure, in which the reaction signal is taken from the eye by means of an electrode represented with its progress over time and evaluated. One-time flashes of light or light-dark sequences (flicker ERG) are used as stimuli. At the same time, the average value for the entire surface of the retina is determined. In recording the potentials evoked, electrodes are applied to a certain point on the head and the signal measured corresponds to the reaction, which occurs through bundles of nerve fibers at the measuring position. Details on this have been published by J. J örg and H. Hielscher in the book "Potentials Evoked in Clinic and Practice," Springer Publishing House.

To determine the topology of the retinal sensitivity, the possibility exists basically of stimulating surface segments of the retina with individual light stimuli aimed at surface segments and measuring the reaction. Since average values must be formed in order to reduce measurement error, this process results in an intolerably long measuring time.

In U.S. Pat. No. 5,382,987, the coupling of an ophthalmoscopic device on the basis of a three-way Maxwell observation system is suggested for the optical examination of the retina of the eye, with a perimeter arrangement to determine the field of vision, where the spectral sensitivity of a selected portion of the retina can be measured with the aid of the electroretinogram, for which a stimulus pattern is transferred to the retina. With this process, the sensitivity of an individual portion, as well as the overall picture of the retina, can be examined. For the measuring examination of all parts of the retina, this would also result in an intolerably long examination time.

The use of a laser projector, provided with an optical modulator for the generation of a brightness pattern on the retina for the measurement of the pattern electroretinogram (PERG), is provided by Daniel R. Peters and John Tabora in the U.S. Pat. No. 5,233,373. With this, however, only a selected surface of the retina can be examined and the examination of multiple surfaces can be done only sequentially.

An improved process in the associated system for determining the distribution of functions of the reaction to stimuli over the surface of the retina was provided by R. Richardson in EP 0 375 737. Here, the overall reaction of the retina to stimuli in the field of view is recorded, where the stimuli are formed by series of patterns whose intensity changes in both horizontal and vertical directions. As an example, a sine or cosine wave distribution of intensity is used and, by back transformation from the measured overall signals, the distribution of sensitivity over the surface of the retina can be calculated. The disadvantage of this process is that measuring errors in the determination of the individual coefficients cannot be recognized, but individual measurement errors affect the calculation of the entire distribution function. Also disadvantageous in this process is the fact that the resolution must be adjusted to the highest density of sensitivity distribution, although it is present only in a narrowly limited range.

In U.S. Pat. No. 5,539,482, a process is given in which the stimulus image consists of multiple rectangles of size increasing outward, whose brightness change is controlled with different frequencies in the range of 10 Hz to 45 Hz. In the example portrayed, 9 rectangles are processed simultaneously, modulated in brightness and the signal measured is evaluated with the aid of a Fourier transformation. The advantage of the process lies in the fact that, by measuring the Nyquist frequency, the effects of the lower ganglia cell layers can be detected. It is disadvantageous that, for the determination of the Nyquist frequency, multiple measurements must be carried out with varying distributions of modulation frequencies and that the measuring time for each frequency distribution must be chosen to be long enough for unambiguous results to be determined for the individual frequencies. It is stated that an expansion to up to 32 "zones" is possible. As a result, the process, even if it is so expanded, still has a very low resolution with respect to the surface segments, which can be examined.

Another process was indicated by E. E. Sutter and D. Tran in the magazine Vision Research (Great Britain), Vol. 32, No. 3, pp. 433–446, 1992, with which relatively good results have been achieved. To determine the topography of the ERG components, a digital process is used, in which hexagons are used as stimuli, whose variations in brightness over time are controlled by m sequences. In this connection, 241 hexagons are used whose size increases from the central point outward. Weighting the signal progression according to the average value for the corresponding range of surface segments and interfering with the determination of the amplitude contained in the signal progression reduces the useful signal. For the measurement, m sequences with a length of 65,535 steps are used, which are always displaced from each other by 256 steps. At the image change frequency of 67 Hz, there is a total measurement duration of about 16 minutes, where the measurement was subdivided into 32 time intervals, each of which lasted 30 seconds, plus time for overlap. The first disadvantage is that the process can deliver exact results only to the extent that the reaction function of the retina also reacts linearly to the stimuli. This connection is, however, only partial in the case of an image repetition frequency of 67 Hz, and then only present if there is a short after-glow on the picture tube. A further disadvantage of this process consists in the fact that the signal change must be monitored subjectively and, if recognizable problems arise, for example as a result of blinking, or in the case of contact problems with the electrodes, the associated time interval must be repeated. The most substantial disadvantage is, however, that there is no possibility of judging intermediate results of the individual time intervals and that only at the end of the measurement, that is, when measurement values are available covering all time intervals, the possibility exists of determining a result and evaluating this result so that, in the case of unnoticed problems, the entire measurement must be repeated.

In the U.S. Pat. No. 4,846,567, E. E. Sutter already gave a basic principle of the process in which, as stimuli, a display with a quadratic array of elements which can be activated is used, where the brightness changes of the elements over time are controlled by m sequences. The calculation of the individual reaction signals is done with the aid of the cross-correlation function. Here, also, m sequences of the length $2^{16}-1=65,535$ is used, which are offset from one another by 256 steps. It is also suggested that the entire measurement be subdivided into time intervals of about 20 to 40 seconds. As a result, the principle corresponds in all substantial points to the process as used in the magazine Vision Research, and contains the same disadvantages as in the above-mentioned publication.

The purpose of the invention is to create a process and a system with which the topography of the retinal reactions can be determined with high effectiveness and great safety, where intermediate results can be evaluated, in order to take into consideration only those intermediate results which are recognized as qualitatively good, so that both the operating personnel and the patient are disturbed as little as possible, and where the process and the device can also be adapted to special examinations.

In accordance with the invention, the problem is solved by the characteristics named in Claims 1 and 15. Advantageous embodiments are given in the subclaims.

The advantage of the solution in the invention consists in the fact that equal discrete time intervals are used for the measurements, and that the quality of the partial results determined for each time interval can be evaluated so that only partial results which have been found to be good are used for the further evaluation. Any measurement errors which occur can be recognized immediately, and it is not necessary to repeat the entire measurement consisting of multiple time intervals, but only further partial results must be determined by one time interval. Since equal time intervals are always used, their number can be chosen as desired, that is, if uncertainties arise, the precision can be improved by the adding of further time intervals. It is also advantageous that the signal is monitored for limit values in the total eye reaction and, if the m sequences exceed limits, it can be set back by a predeterminable number of sets and the signals for the total eye reaction can be replaced by the repeated values.

With the adjustable duration for the first partial step, in which the image defined by the m sequence is displayed, and the second partial step, in which the surface is made dark, the device can be adjusted for the measurement of selected reactions of the retina of the eye.

The solution in accordance with the invention will be explained in greater detail on the basis of a sample embodiment. In the associated drawings.

Figure 1:
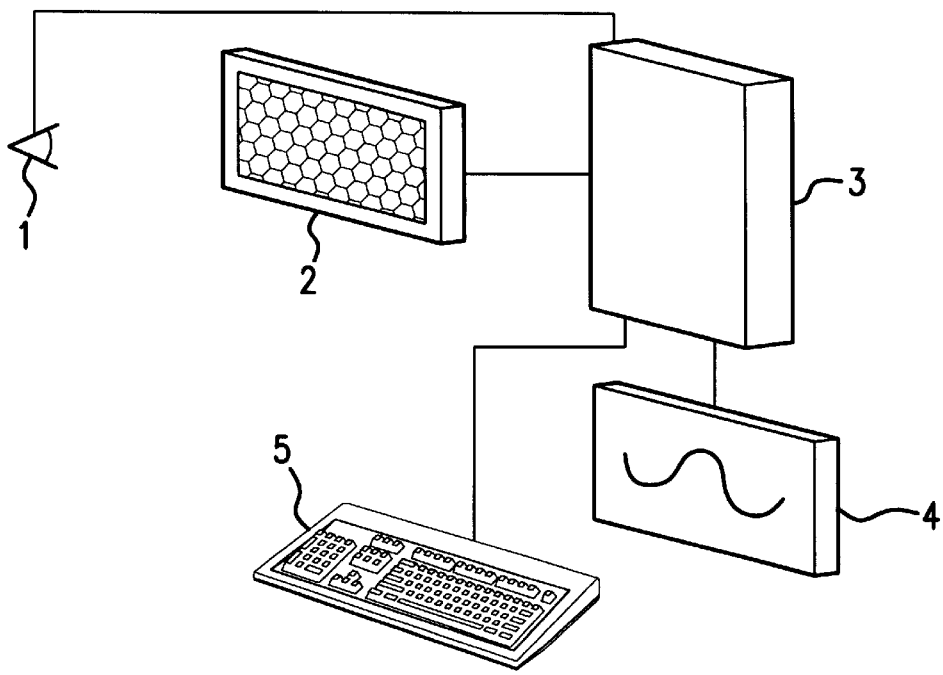
FIG. 1 shows the design in principle in accordance with the invention.

FIG. 1 shows the structure in principle of the system used for the measurement. An eye 1 of the patient looks at a surface 2 on which the glowing image is represented, consisting of a number N of surface segments. The bright and dark control of the surface segments is done through a control unit 3. The operation, that is, the adjustment of the measuring parameters, is done with a keyboard 5 connected to the control unit 3. Operator control is exercised through an indicator unit 4 connected to the control unit 3, and the results are displayed. The reaction signal taken from the eye 1 is fed into the control unit 3 for evaluation.

Figure 2:
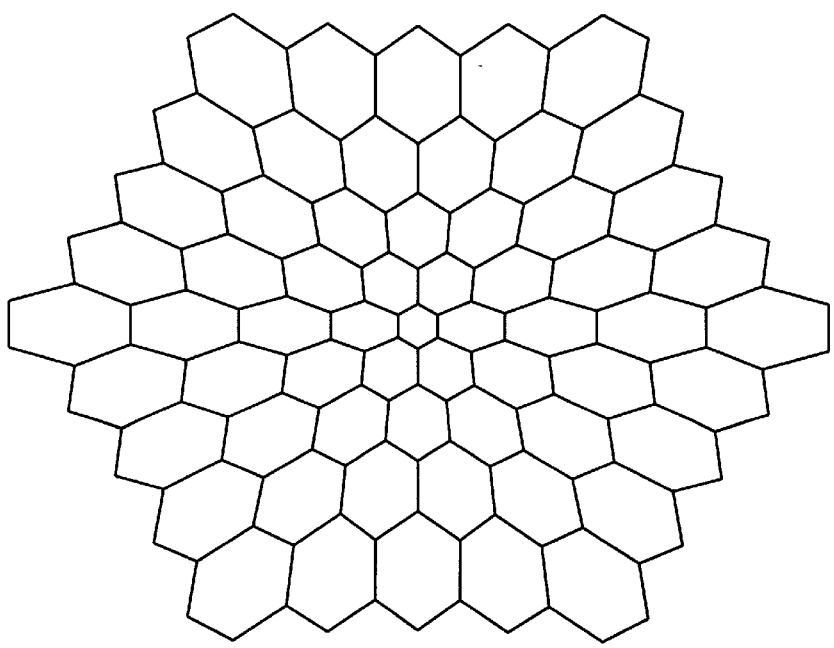
FIG. 2 shows an image with 61 surface segments consisting of hexagons.
Figure 3:
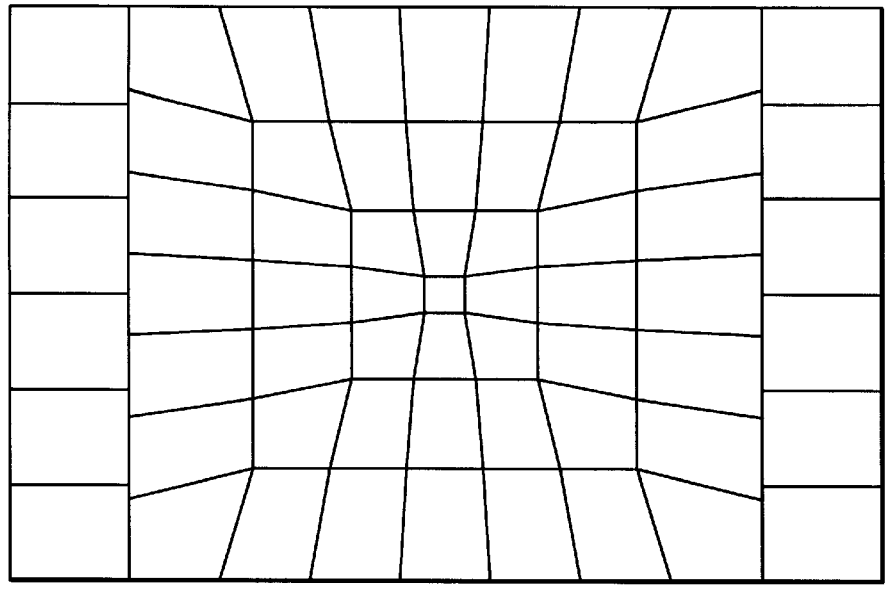
FIG. 3 shows an image with 61 surface segments consisting of rectangles.
Figure 4:
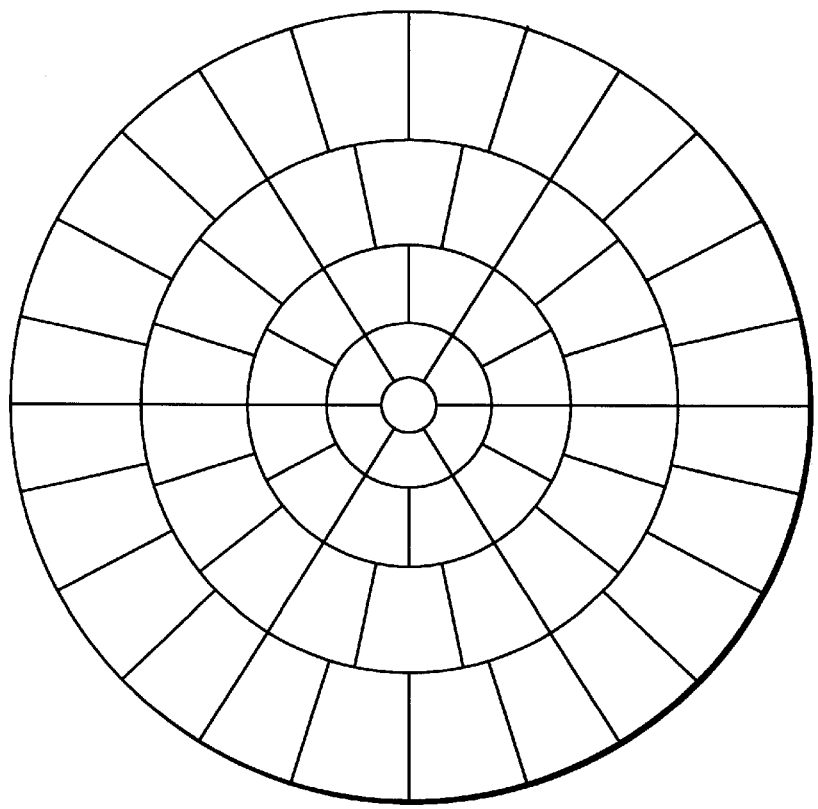
FIG. 4 shows an image consisting of circular ring segments with 61 surface segments.

Images are represented on the surface 2, which consists of limited surface segments with size increasing from the center outwards. As an example, with N=61 surface segments, FIG. 2 shows an image consisting of hexagons, FIG. 3 shows one consisting of rectangles and FIG. 4 shows one with circular ring segments.

The bright and dark control of the surface segments is done by m sequences, as a result of which the reaction functions of all surface segments can be calculated from a single reaction signal taken from the eye. m sequences are formed in which a single coefficient is divided by an non-reducible primitive polynomial using binary modulo-2 division. In the case of a polynomial of degree g, a periodic result with a period length L is therefore generated. In this connection, the relationship between period length L and degree g of the polynomial applies:

$$L=2^g-1 \tag{a}$$

For purposes of illustration, the calculation will be carried out with the polynomial of the degree g=3. If, for example, the polynomial $$P(x)=x^3+x+1$$

and the coefficient $x^{15}$ are selected, then the following results:

$x^{15}: x^3 + x + 1 = x^{12} + x^{10} + x^9 + x^8 + x^5 + x^3 + x^2 + x + x^{-1} + x^{-4} + x^{-5} + x^{-6} + \ldots$ $$\begin{array}{llll}
x^{15} & +x^{13} & +x^{12} \\
& x^{13} & & +x^{11} & +x^{10} \\
& & x^{12} & & +x^{10} & +x^9 \\
& & & x^{11} & & +x^9 & +x^8 \\
& & & & x^8 & +x^6 & +x^5 \\
& & & & & x^6 & +x^4 & +x^3 \\
& & & & & & x^5 & +x^3 & +x^2 \\
& & & & & & & x^4 & +x^2 & +x \\
& & & & & & & & x & +x^{-1} & +x^{-2} \\
& & & & & & & & & x^{-1} & +x^{-3} & +x^{-4} \\
& & & & & & & & & & x^{-2} & +x^{-4} & +x^{-5} \\
& & & & & & & & & & & x^{-3} & +x^{-5} & +x^{-6}
\end{array}$$

If the results for all occupied coefficients are represented by 1 and for all unoccupied coefficients by 0, then, taking into account that the coefficients $x^{14}$ and $x^{13}$ are null, the following results from the sequential placement of the coefficients, and:

<u>0001011</u> <u>0010111</u> <u>0010111</u>...
1st period   2nd period   3rd period A period is then designated as an m sequence or a maximum length sequence. Of each m sequence of the length L, exactly L sequences can be formed cyclically displaced by one step, and if one designates the m sequence as $S_i(0, 1)$, then the following applies:

$S_0(0, 1) = 0\ 0\ 1\ 0\ 1\ 1\ 1$ $S_1(0, 1) = 1\ 0\ 0\ 1\ 0\ 1\ 1$ $S_2(0, 1) = 1\ 1\ 0\ 0\ 1\ 0\ 1$ $S_3(0, 1) = 1\ 1\ 1\ 0\ 0\ 1\ 0$ $S_4(0, 1) = 0\ 1\ 1\ 1\ 0\ 0\ 1$ $S_5(0, 1) = 1\ 0\ 1\ 1\ 1\ 0\ 0$ $S_6(0, 1) = 0\ 1\ 0\ 1\ 1\ 1\ 0$ $S_7(0, 1) = S_0(0, 1)$

Correspondingly, the negated m sequence results with the same characteristics:

$/S_0(0, 1) = 1\ 1\ 0\ 1\ 0\ 0\ 0$

For algebraic calculations, the following substitution is carried out in the m sequences:

$0 \rightarrow -1$ and $1 \rightarrow +1$ and the thus-formed negated m sequence is designated:

$/S_0(-1, +1) = +1+1-1+1-1-1-1$

If one forms the discrete cross-correlation coefficients KKK from two m sequences displaced from each other by n steps, through all steps s of the m sequence with the length L, then $$KKK(/S_i, /S_{i+n}) = \frac{1}{L}\sum_{s=0}^{L-1} /S_i(-1, +1) \cdot /S_{i+n}(-1, +1) \quad \text{(b)}$$

then there results for a displacement by n=0 steps:

KKK=1 and for all other displacements by n≠0 steps:

KKK=−1/L as can easily be proven for the example with L=7. The results for n≠0 represents a residual error which can be eliminated by inserting a step +1 in all m sequences $/S_i(-1, +1)$, at any point but at the same point in each.

Figure 5:
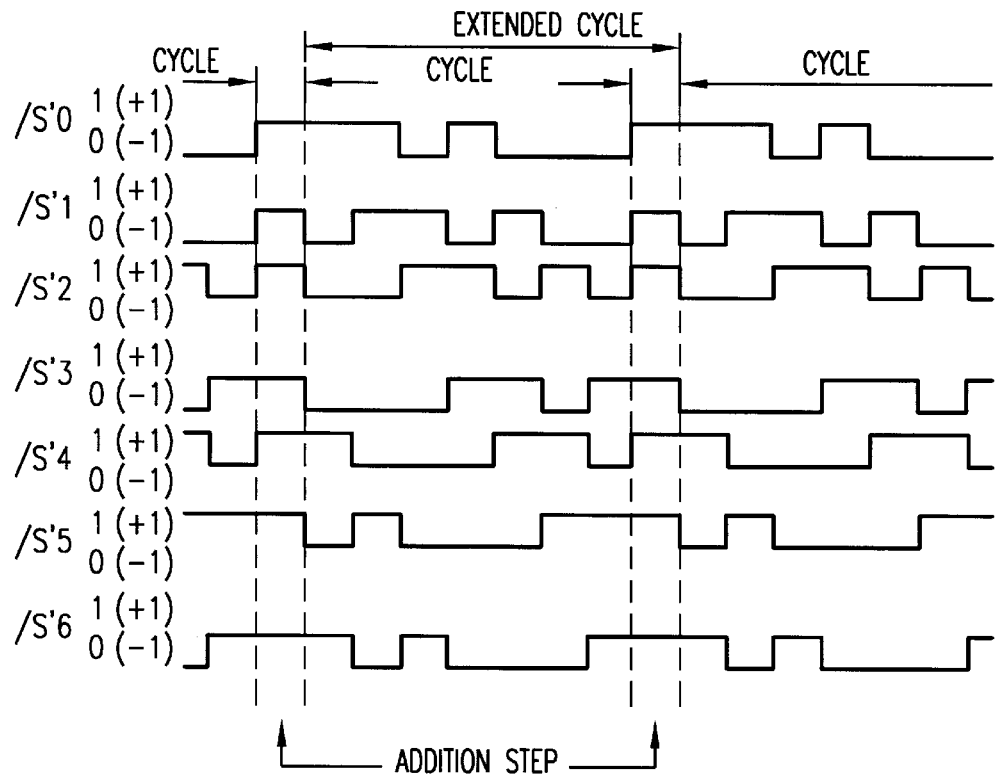
FIG. 5 shows the signal changes in length and m sequences with the length L'=8 and FIG. 6 shows the correspondence between the surface segments and the total signals.

The extended m sequence thus formed $/S_i'(-1, +1)$ is represented in FIG. 5. The cross-correlation coefficients have, for the extended m sequences, the values:

$n = 0: KKK' = 1 \quad n \neq 0: KKF' = 0$ if L is replaced by L'=L+1. For the length, with equation (a), the following applies:

$L' = 2^g \quad \text{(c)}$

Now if the m sequences $/S_i'(0, 1)$ are used for the bright-dark control of the surface segments and each of the n surface segments generates a partial reaction proportional to the brightness $f_i(/S_i'(0, 1))$, then the entire reaction signal is:

$$F(/S) = \sum_{i=0}^{N} f_i(/S_i'(0, 1)) \quad \text{(d)}$$

With the cross-correlation calculation KKR, the corresponding signal components can again now be extracted from this signal for each m sequence used for bright-dark control with the displacement i:

$$KKR'(F(/S), /S_i'(-1, +1)) = \qquad (e)$$

$$\frac{1}{L}\sum_{s=0}^{L-1} F(/S) \cdot /S_i'(-1, +1) = \frac{1}{2}(f_i(1) - f_i(0))$$

That is to say, in this manner each of the partial functions can be recovered error-free from the signal mixture. This applies, however, only when proportional relationships between the functions are involved.

If the reaction signal of the surface segments is a time-dependent partial function sequence, especially one dependent on brightness changes $\phi_i(\tau_1/S_i'')$, then the total reaction signal for N surface segments is:

$$\Phi(\tau, /S'') = \sum_{i=0}^{N} \varphi_i(\tau, /S_i''(0, 1))$$

If, at each step of the m sequences, a new partial function sequence $\phi_i(\tau_1/S_i'')$ is triggered, then with the aid of the cross-correlation function KKF the partial function sequences contained in the complete signal can again be calculated:

$$KKF(\Phi(\tau, /S''), /S_i''(-1, +1) = \qquad (f)$$

$$\frac{1}{L}\sum_{i=1}^{L-1} \Phi(\tau, /S''), /S_i''(-1, +1) = \frac{1}{2}\varphi_i(\tau, /S_i''(0, 1)$$

The result remains error-free, even in the case of non-linear relationships, if the minimum time displacement $\Delta t$ is greater between the m sequences than the duration $T_{max}$ of the function sequence $\phi_i(\tau_{1/Si}'')$ or if the partial reactions triggered are superimposed linearly.

However, the eye reaction signal is dependent upon the bright or dark adaptation of the eye, as well as the intensity and the duration of the light stimulus. The superposition of the signals from multiple stimuli following one after the other is approximately linear only after a certain time interval between the stimuli. With the cross-correlation function KKF, a result which is, to a great extent, error free is achieved only if the individual steps of the m sequences are temporally displaced with respect to one another, far enough for the superposition of the signals of succeeding reactions to occur almost linearly. As a first approximation it can be assumed that, with an average light density, this time is approximately $\delta$=60 ms.

The reaction function recovered from the cross-correlation function KKF has a poorer signal-to-noise ratio by a factor of 2N for the entire surface, in the case of N surface segments, compared to the reaction functions for the total surface in the formation of average values over the same number of measuring steps. In order to improve the signal-to-noise ratio by the factor M, $M^2$ measuring steps must be carried out. For N=61 surface segments and a time interval of about $\delta$=60 ms measuring step, there is a measuring duration of $$T_M = M^2 + \delta = 223 \text{ sec} \sim 4 \text{ min},$$

if M=N.

However, over this period of time, no one can keep his eye absolutely still. Therefore, the measurement is subdivided into 8 time intervals of approximately 30 seconds each, and the total results are obtained by adding the reaction functions of the surface segments over all time intervals.

In order to be able to calculate the partial reactions with equation (f) in each time interval, each segment is given one or more complete extended M sequences. For the values assigned, this results in an M sequence with the cycle length $$L' = 2^g = 512$$

g=9 if exactly one m sequence is provided for a time interval. The individual surface segments are controlled by m sequences which are displaced each by 8 steps from each other. As a result, the time functions of the surface segments have a distance of about 480 ms from one another.

By changing the setting, the cycle length and the step interval can be increased by a factor of 2 or 4 and simultaneously the step duration correspondingly decreased, as a result of which the signal-to-noise interval is improved but the effect of the non-linearities increases. Similarly, the cycle length can be decreased by a factor of 2 or 4 and simultaneously the step length corresponding increased, as a result of which the effect of non-linearity is reduced, but the signal-to-noise ratio is degraded. An improvement is possible here by increasing the number of time intervals.

Every step of the m sequence consists of a first partial step in which the surface segments are turned bright or dark, corresponding to the m sequences, and a second partial step in which all surface segments are darkened. This results in an unambiguous beginning condition for each step, even for the areas of the m sequence which consist of several sequential 1-steps. The time portions of the two partial steps are adjustable.

Each time interval consists of a preset partial cycle during which the start-up processes of the measuring device fade out, a complete cycle for the determination of measured values, and thereafter a partial cycle whose duration is at least as great as the time of the reaction function to be calculated by the cross correlation.

After the measurement is completed in a time interval, the reaction functions of the surface segments are calculated according to equation (f). The results of the measurement of a time interval have a very poor signal-to-noise ratio and can hardly be evaluated individually. Since the reaction signals of the surface segments are, however, very similar, the sum function provides a substantially better signal-to-noise ratio.

Figure 6:
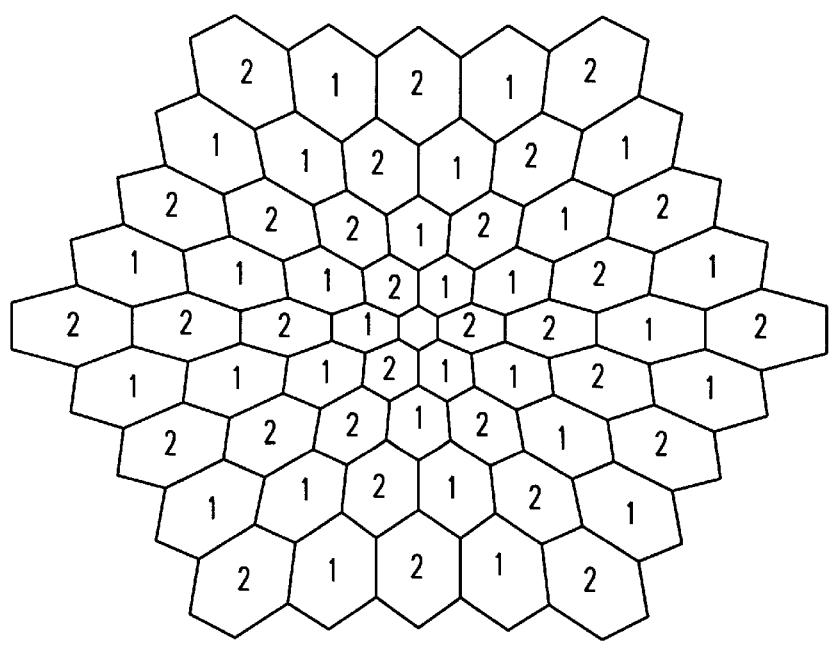

If two partial sums are formed corresponding to the assignment of the partial surfaces, in accordance with FIG. 6, then measurement errors and interference become noticeable in the two sum functions through differences, since the number of the components weighted with +1 and −1 in the two partial sums is different. By comparing the two functions with each other and with the results of previous or subsequent time intervals, the quality of the measurement results of the individual time intervals can be determined. For the evaluation, only the results recognized as good are used, with the reaction functions of the surface segments being added. At the same time, the number of time intervals used for evaluation can be increased as desired, since in each time interval a complete partial result with a poor signal-to-noise ratio is determined, but improved by averaging.

A picture tube can be used to represent the image consisting of surface segments. In another embodiment, the image is generated on a surface populated with LEDs. Similarly, in another embodiment, a laser projector can be used, whose beam is deflected in two dimensions for the representation of the image. The most flexible time control is possible with the surface populated with LEDs. Both the picture tube and the laser projector write the image serially and the duration of time for the partial steps for the representation of the image and the partial step in which all surface segments are blacked out is only adjustable as an integer multiple of the image representation time and by changing the image repetition frequency. For the evaluation of the reaction generated, it must be taken into account that the laser projector actually generates an ideal serial flash image and a picture tube a longer flash corresponding to its afterglow. In the case of the surface populated with LEDs, a defined on-time duration is achieved.

The eye reaction signals are derived from a differential amplifier placed inside or outside the control unit, whose first input is connected with an electrode placed at or in the immediate vicinity of the eye and whose second input is connected to an electrode which is placed at an electrically neutral spot, for example, the forehead of the patient. The signal measured is fed into an adjustable band pass of the control unit 3 in order to suppress interference signals outside the frequency range to be measured.

Interference which arises, for example through blinking, can be recognized by monitoring the amplitude, which reacts to both the upper limit of amplitude and the lower limit of amplitude during a certain time period. In order to avoid having to repeat the entire measurement, at least for the time interval involved in the case of such an error, the m sequences are retarded directly after recognition by a preset number of steps. The number of the sets to be retarded r should be r≧g, where g is the degree of the polynomial with which the m sequence is generated.

For the measurement, the signals of the magnetoretinogram or visually evoked potentials (VEP) can be used.

With the process represented, the topology of the eye reaction can be determined with even higher resolution than those represented in FIG. 2, FIG. 3 or FIG. 4. In a first variant, the image is subdivided into multiple segments lying symmetrically from the center point and the individual segments are measured, one after another, where each segment has approximately 61 surface segments. Similarly, the image consisting of a larger number of smaller surface segments can be measured in multiple stages, by using for the measurement different surface segments distributed over the entire surface, analogous to FIG. 6. Similarly, images which consist of multiple smaller surface segments can be measured with a consistent measurement over a greater period of time. In this connection, corresponding to the number of surface segments, longer m sequences are used and the quality is evaluated for groups of associated time intervals.

The control unit 3 consists of a computer which both generates the digital cyclic time signals for the control of the figure consisting of surface segments and evaluates the measurement data as well as controlling the operation of the system and portraying the results. An advantageous embodiment results if the control unit 3 consists of two computers coupled together, where the first computer serves to generate cyclical time signals for the control of the image consisting of surface segments and the evaluation of measurement data and the second computer is used for operating the system and the portrayal of results.

The core of the invention consists in the fact that, for each time interval, as a digital time function of the bright and dark control of the surface segments complete, preferably negated m sequences extended by one step, are used, as a result of which for each time interval the reaction functions for all surface segments are calculated by forming the cross-correlation function. As a result, it is possible to evaluate the measurement result for each time interval and only good measurements are brought in for the formation of the end result.

We claim:

1. A process for determining the topography for bioelectrical eye reaction signals to light stimuli, depending upon the location of each light stimulus on the retina, with a surface placed before the eye, on which a light emitting image is portrayed for the stimulation, consisting of surface segments, where each surface segment is lighted and darkened, depending upon a digital time function assigned to it, and at the same time the total reaction of the eye is measured and in which, from the total reaction of the eye, by calculating the cross-correlation function with the digital time function, the components of the reaction functions of the eye assigned to each surface segment is determined, where, for the measurement, any number above a minimum value of similar time intervals, closed in themselves, is used, each of which provides a partial result which can be evaluated, in connection with which, for each time interval, complete m sequences are used, as a digital time function, preferably negated and extended by one additional step, where for each surface segment the same m sequence cyclically displaced by at least one step is used, and the additional step is inserted in all m sequences, in parallel at the same point in time and, for each time interval, the reaction function of each surface segment is calculated by forming the cross-correlation function and by adding up the reaction functions of multiple surface segments, at least one sum function is formed, with which the quality of the measurement of the time interval is evaluated and, an overall function is formed for each surface segment for further use, in order to reduce measurement errors by adding up the reaction functions for each measurement evaluated as good for a time interval.

2. The process of claim 1, in which each step of the extended m sequence consists of a first partial step in which the surface segments corresponding to the negated m sequences are brightened and darkened, and a second partial step in which all surface segments are darkened, that the duration of the two partial steps is adjustable and that, for the calculation of the cross-correlation function, the corresponding function value of the m sequence of the first partial step is used for each surface segment for the complete time of the reaction function to be calculated.

3. The process of claim 1 or 2, in which the signal for the total eye reaction is monitored for exceeding limit values, and, when limit values are exceeded, the m sequences are set back by an adjustable number of sets and the signals for the total eye reaction are replaced by the values repeated.

4. The process of claim 1 or 2, in which multiple functions are formed from an equal number of surface segments for the evaluation of the quality of each measurement, where different surface segments are assigned to each function distributed over the total area and that the functions are compared to each other and to the functions of the preceding or successive measurements, and their similarity is used to measure the quality of the measurement.

5. The process of claim 1 or 2, in which every measurement to be carried out over a time interval consists of a preceding partial cycle to allow start-up oscillation processes to fade out, of the time interval for the determination of the partial result, and of a succeeding partial cycle which is at least as long as the duration of the reaction function to be calculated.

6. The process of claim 1 or 2, in which the image is formed in a known manner of hexagons increasing in size from the center outward.

7. The process of claim 1 or 2, in which the image is formed of rectangles increasing in size from the center outward.

8. The process of claim 1 or 2, in which the image is formed of circular ring segments increasing in size from the center outward.

9. The process claim 1 or 2, in which only segments of the surface are used to portray preferably smaller surface segments and the other segments of the surface remain set to a constant brightness over the duration of the measurement, in order to examine parts of the retina with higher resolution.

10. The process of claim 1 or 2, in which the surface segments emit light of a single color which can be preselected.

11. The process of claim 1 or 2, in which the signal for the total eye reaction, which consists of the total of the individual reactions of all surface segments, is obtained through an amplification and limitation of the frequency band.

12. The process of claim 1 or 2, in which the total eye reaction is determined by electroretinography.

13. The process of claim 1 or 2, in which the total eye reaction is determined by magnetoretinography.

14. The process of claim 1 or 2, in which the total eye reaction is determined by the measurement of potentials evoked which are taken from the corresponding spots on the head.

15. A system for carrying out the process in accordance with claim 1 for determining the topography for bioelectrical eye reaction signals to light stimulation, as a function of the location of each light stimulus on the retina, with a device (2) placed before the eye for the representation of a light emitting image consisting of surface segments, which is connected with a control unit (3), in order to brighten and darken the surface segments, and in which means are provided to feed the reaction signal taken from the eye (1) to the control unit, which also includes a display unit (4) for operation by the operator and the display of results, as well as a keyboard (5) to operate the system, both of which are also connected to the control unit and that the control unit includes means to generate complete m sequences, preferably negated and extended by a supplementary step, which are cyclically displaced for each surface segment by at least one step, and in which the supplementary step is added to all m sequences in parallel at the same point in time, and that the control unit (3) also is provided with means to calculate the cross-correlation functions from the reaction signal extracted from the eye (1) and the m sequences, with which the reaction functions are determined for all surface segments, and that the control unit (3) includes means for evaluating the quality of the measurement.

16. The system of claim 15, further comprising means to brighten or darken the surface segments during a first partial step corresponding to the function value of the current m sequence and, during a second partial step, to darken all surface segments, wherein the duration of these two partial steps is adjustable.

17. The system of claim 15 or 16, in which means for measuring and monitoring of the changes in the signal for the total eye reaction which, when limit values are exceeded, affect the means for generating the m sequences in such a manner that all m sequences are set back a presettable number of steps and the defective measured values are replaced by the repeated values.

18. The system of claim 15 or 16, in which the light emitting image consisting of segments comprises a picture tube.

19. The system of one of the claim 15 or 16, in which the surface segments of the light emitting image are populated with light emitting diodes.

20. The system of one of the claim 15 or 16, in which the surface segments of the light emitting image are irradiated by an LCD projector.

21. The system of one of the claim 15 or 16, in which the light emitting image consisting of surface segments comprises a surface irradiated by a laser.

22. The system of one of the claim 15 or 16, in which the signals for the total eye reaction are fed into the control unit (3) through an amplifier with upper and lower limit frequency which can be set through the control unit (3) and an analog/digital converter and a sampling circuit controlled synchronously with the display of the image, whose output connections are connected to a computer for further processing, and that in the control unit (3), means are provided for the setting of the limit frequencies of the amplifier.

23. The system of one of the claim 15 or 16, in which the control unit (3) includes means for storage and display of the changes over time of the signals of the total eye reaction.

24. The system of one of the claim 15 or 16, in which the control unit (3) includes means for displaying the changes over time of the functions formed over multiple surface segments.

25. The system of one of the claim 15 or 16, in which the control unit (3) includes means for displaying the reaction signals and their amplitudes determined for the surface segments.

26. The system of claim 15 or 16, in which the control unit (3) includes at least one computer, and that the generation of the digital cyclic time signals for the control of the image consisting of surface segments, the evaluation of the measurement data and the operation of the system and the display of results is done through this computer.

27. The system of claim 15 or 16, in which the control unit (3) includes two computers, where the generation of the digital cyclical time signals for the control of the image consisting of surface segments and the evaluation of the measuring data is done by the first computer, which is coupled to the second computer for the operation of the system, the evaluation and display of results.

* * * * *